(12) United States Patent
Collard

(10) Patent No.: US 6,707,870 B2
(45) Date of Patent: Mar. 16, 2004

(54) METHOD FOR DETERMINING FRICTION FORCES OCCURRING ON AN OBJECT MOVING IN A GUIDE ON AN INACCESSIBLE SITE

(75) Inventor: Bruno Collard, Manosque (FR)

(73) Assignee: Commissariat a l'Energie Atomique, Paris (FR)

(*) Notice: Subject to any disclaimer, the term of this patent is extended or adjusted under 35 U.S.C. 154(b) by 0 days.

(21) Appl. No.: 10/148,645

(22) PCT Filed: Nov. 29, 2000

(86) PCT No.: PCT/FR00/03331
§ 371 (c)(1),
(2), (4) Date: Sep. 16, 2002

(87) PCT Pub. No.: WO01/40768
PCT Pub. Date: Jun. 7, 2001

(65) Prior Publication Data
US 2003/0076916 A1 Apr. 24, 2003

(30) Foreign Application Priority Data
Nov. 30, 1999 (FR) .............................................. 99 15066

(51) Int. Cl.$^7$ ................................................ G21C 17/00
(52) U.S. Cl. ................ 376/258; 376/245; 376/219; 376/236; 376/240; 376/242; 376/234
(58) Field of Search ................................ 376/245, 219, 376/258, 236, 240, 242, 234

(56) References Cited

U.S. PATENT DOCUMENTS 4,983,350 A    1/1991   Foret ........................ 376/245

FOREIGN PATENT DOCUMENTS

DE    250 201 A1    9/1987    ............ G21C/17/00
EP    0 206 877     6/1986    ............ G21C/7/26

OTHER PUBLICATIONS

Björnkvist et al., "Application of a Semi–Empirical Rod Drop Model For Studying Rod Insertion Anomalies At South Texas Project and Ringhals Unit 4", pp. 81–89.

Shinohara et al., "Behavior of an Elastic Rod Falling Into A Vibrating Circular Cylinder", Apr. 1984, Bulletin of JSME, vol. 27, No. 226, pp. 794–801.

Primary Examiner—Harold J. Tudor
Assistant Examiner—John Richardson
(74) Attorney, Agent, or Firm—Thelen Reid & Priest LLP

(57) ABSTRACT

With this method it is possible to evaluate opposing friction forces occurring after a certain operating time on a mobile object in a guide.

The method consists of measuring the variations in the speed of movement of the mobile object, of calculating the theoretical speed of movement without friction, of combining these two results and thereby deducing outside opposing forces through calculation of the acceleration of the mobile object.

Particular application to the evaluation of additional friction forces acting on a mobile control cluster assembly in the core of a pressurized water nuclear reactor.

2 Claims, 3 Drawing Sheets

METHOD FOR DETERMINING FRICTION FORCES OCCURRING ON AN OBJECT MOVING IN A GUIDE ON AN INACCESSIBLE SITE

AREA OF THE INVENTION

The invention arises from the measurement of forces, friction forces in particular, acting on a moving object in a guide and inaccessible to an operator. The main application of this method is the measurement of forces acting on a mobile assembly formed of the control rod and cluster of control rodlets commonly called: "control cluster", inserted in the fuel assembly of a pressurized water nuclear reactor.

PRIOR ART AND PROBLEM RAISED

The neutron activity in the core of a pressurized water reactor is regulated by the controlled use of control clusters inserted downwards into fuel assemblies to shut down nuclear activity. The safety of pressurized water reactors therefore partly depends upon the proper functioning of the control clusters. For example, an emergency stoppage of the nuclear reactor requires the dropping under gravity of the control clusters within a given time period, in the order of two seconds but depending on the type of reactor. Each cluster descends into the core of the reactor under gravity, the travel distance in the order of four metres being finally halted by a buffer.

During required programmed maintenance operations, to change fuel rod assemblies or control clusters, tests are needed to conduct measurements in order to control the functioning of these control clusters. A certain number of operating circumstances, such as deformation of fuel assemblies, wear of control cluster guides, the presence of foreign bodies, deformation or swelling of the control cluster or control rods, excessive flow rate in the fuel assemblies, transverse flow of water in the plenum, may deteriorate the dropping under gravity of the control clusters and therefore accelerate or delay their downward movement or even cause its obstruction. It follows that it is therefore necessary and essential to have permanent knowledge of induced forces whether parasitic or not, under these special or deteriorating conditions, and their position along the travel pathway.

However this entire mechanism of control clusters, their guide and their control rod, is located within the very containment of the core of the reactor and is therefore inaccessible to human operators. Similarly, materials including this assembly of reactor equipment, are installed within this containment. It is therefore impossible to control their functioning or to ascertain degradation through human action or by retrieval of the equipment to be inspected.

One measurement device that is very frequently used to control the movement of control clusters is a rod position indicator (RPI), able to measure either movement or speed of movement. It is to measure speed of movement that the RPI is used in the event described above.

It has been customary, up until the date of filing of the present patent application, to measure and record the dropping speed of the cluster and its end-of-travel slowing. Should a substantial increase in the slowdown time be recorded, in accordance with preset criteria, a decision is taken to change the faulty equipment. Laboratory tests, non contaminated, may help to improve these measurements and controls but cannot reproduce the exact conditions prevailing within the containment of the reactor core.

Moreover, measurement of the change in dropping speed (called "fall kinematics") remains approximate using this rod position indicator (RPI).

The purpose of the invention is to overcome these disadvantages by determining a method for evaluating or determining the friction forces acting on the lowering of a control cluster, this method being reliable for managing the operating efficiency of the control clusters and optionally organizing their change or replacement or the change and replacement of fuel assemblies. The achievement of this purpose will therefore provide improved management of the core of a pressurized water reactor.

SUMMARY OF THE INVENTION

For this purpose, the main subject of the invention is a method for determining friction forces occurring on a moving object in a guide, by means of a speed sensor, and comprising the following steps:

1) measuring and recording changes in the velocity of the object initially before the occurrence of friction:

$$V_1 = f_1(t)$$

wherein $V_1$ represents the velocity of the object before friction occurs, and $f_1$ is a function of time (t).

2) calculating distance of travel $d_1$ with integrated change in velocity of the object before the onset of friction, to obtain the change in velocity $V_1 = g_1(d)$ in relation to distance of travel:

$$d_1(t) = \int_{u=0}^{t} V(u)\,du;$$

wherein g1 is a second function of distance (d), and (u) is a time value.

3) measuring and recording the change in velocity of the object after the onset of friction:

$$V_2 = f_2(t);$$

4) calculating distance of travel with integrated change in velocity of the object, after the onset of friction, to obtain the change in this velocity $V_2 = g_2(d)$ in relation to distance of travel:

$$d_2(t) = \int_{u=0}^{t} V_2(u)\,du;$$

5) calculating the difference between the two velocitaies in relation to travel before and after onset of additional friction $V_3 = (g_1 - g_2)(d) = g_3(d)$;

6) calculating the change in velocity of the object in relation to travel, before the onset of friction, using a predetermined calculation programme:

$$V_4 = g_4(d)$$

7) subtracting from this change $V_4$ the difference $V_3$ in measured speed changes, $V_5 = V_4 - V_3 = g_5(d)$; and 8) deducing, by differentiation between $V_4$ and $V_5$ and multiplication by the weight M, the additional friction forces acting on the movement of the object:

$$F_{additional} = M(\gamma 5 - \gamma 4) = f(d).$$

in which $$\gamma_i = \frac{dV_i}{dt},$$

γ is the acceleration of the object, and the subscripts 2, 3, 4, 5 associated with each symbol represent four successive values of the calculating process.

The chief application concerns measurement of the dropping of a rod control cluster assembly into a pressurized water nuclear reactor, the moving object being a control rod and a control cluster, the speed sensor being a rod position indicator and the guide being the lowering channel.

LIST OF FIGURES

The method according to the invention will be better understood on reading the following description of an embodiment accompanied by several figures in which respectively:

DETAILED DESCRIPTION OF AN EMBODIMENT OF THE INVENTION

Figure 1:
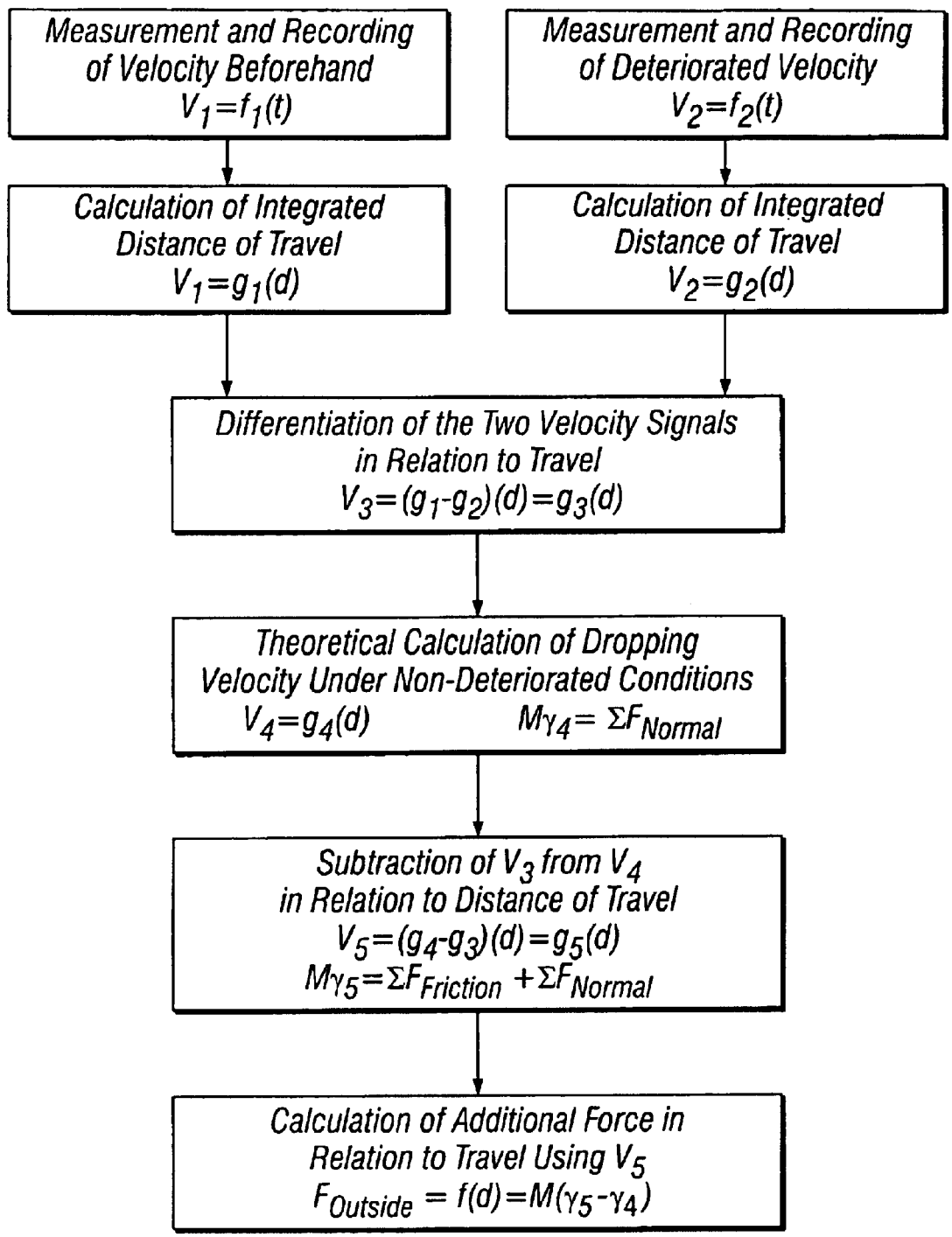
FIG. 1 is a flow diagram of the steps of the method according to the invention.

The present description of the method of the invention is made in its application to the measurement of the lowering of a control cluster into a pressurized water nuclear reactor. The lowering channel is made up of guide tubes, a cluster guide, the heat sleeve, an adapter, the mechanism casing and the rod sheath.

Step n° 1 of the method of the invention is a measuring and recording step. It takes place at the time of start-up of the reactor, that is to say before use of the control rods. The equipment is assumed to be perfectly new and unused, with no opposing force that is not provided by the mechanism disturbing the functioning of the control cluster. This measurement is therefore a reference measurement. In this case a rod position indicator (RPI) is used. More exactly, it is used here to measure the instantaneous lowering velocity of the assembly in relation to time, that is to say $V_1 = f_1(t)$.

Step n° 2 is a calculation step on the basis of the measurement previously made under step 1. It consists of calculating distance of travel with integrated change in velocity of the object before the onset of friction, $V_1(t)$, for the purpose of obtaining the change in this velocity in relation to the distance of travel d of the mobile assembly:

$$d_1(t) = \int_{u=0}^{t} V(u) du$$

From this equation the formula giving the velocity in relation to travel can be deduced:

$V_1 = g_1(d)$.

The two following steps consist of conducting steps n° 1 and n° 2 but after a certain operating time of the nuclear reactor, when undesired opposing friction forces occur which influence the time and lowering velocity of the mobile control rod assembly.

Therefore, step n° 3, using the rod position indicator RPI, consists of measuring and recording the deteriorated instantaneous velocity $V_2$ in relation to time of the lowering of the mobile assembly.

Step 4 then consists of calculating distance of travel with integrated velocity change of the mobile assembly using the measurement made of instantaneous velocity $V_2(t)$. The distance of travel can then be obtained, by integration:

$$d_2(t) = \int_{u=0}^{t} V_2 u(du)$$

From this, the velocity of the mobile assembly can be deduced in relation to distance of travel after the onset of friction forces, that is to say:

$V_2 = g_2(d)$

With step 5 it is possible to obtain the difference in lowering velocity of the mobile assembly before and after the onset of additional friction forces. All that is needed is to calculate the velocity difference $V_3 = (V_1 - V_2) = (g_1 - g_2)(d) = g_3(d)$ in relation to distance of travel d. To make this calculation, the reactor must be under the same operating conditions.

Having regard to the fact that the behaviour of the measuring instrument is not fully controlled, in this case the rod position indicator RPI, since it is installed in a non-accessible containment where no human operation is possible, it was decided only to use this indicator after calculating the difference at step 5. It can indeed be considered that this measuring instrument may behave abnormally and give deformed measurement signals. Particular allusion is made here to data transmission problems which are relatively constant when the rod position indicator is installed. These problems are due in particular to pressure and temperature. On the other hand, it is considered that this deformation peculiar to this measuring instrument is always of the same order.

Therefore, by only using the difference in measurements made before and after the onset of friction forces, any operating default of the RPI is overcome and only the variation in measurements made with this instrument is taken into account. Consequently, in accordance with step 6, the basic magnitude of the lowering velocity of the mobile assembly is calculated using a predetermined calculation code which takes into account known thermohydraulic, mechanical and dimensional conditions before the start-up of the nuclear reactor.

Evidently this calculation code does not take into consideration friction forces occurring after start-up of the reactor, which cannot be predicted. This calculation code therefore gives the theoretical lowering velocity of the mobile assembly under non-deteriorated conditions.

With the code it is therefore possible to obtain the change in theoretical velocity of the mobile assembly $V_4 = g_4(d)$. From this, the sum of normal forces is deduced:

$M\gamma_1 = \Sigma$normal forces

Step 7 consists of taking into account the variations in velocity measured during the first steps and incorporating these in the result calculated during the previous step. This amounts to subtracting from the theoretical velocity, in relation to travel, the difference calculated using the measurements:

$$V_5=(g_4-g_3)(d)=g_5(d).$$

From this is deduced the sum of outside forces:

$$M\gamma_5=\Sigma\text{normal forces}+\Sigma\text{additional friction forces}$$

Step 8, the last step, consists of deducing from the above the outside forces $F_{outside}$ in relation to distance of travel f(d). For this purpose the fundamental equation of dynamics is used.

Using the equation of the balance of forces:

$$M\gamma_4=\Sigma\text{normal forces}$$

$\Sigma$normal forces=assembly-related forces, sheath related forces, guide related forces, other forces.

Each force F is a function dependent upon velocity V, upon distance of travel d, upon system geometry, upon temperature $\theta$ and other parameters, in which:

$$M(\gamma_5-\gamma_4)=\Sigma\text{additional friction forces}$$

Figure 2:
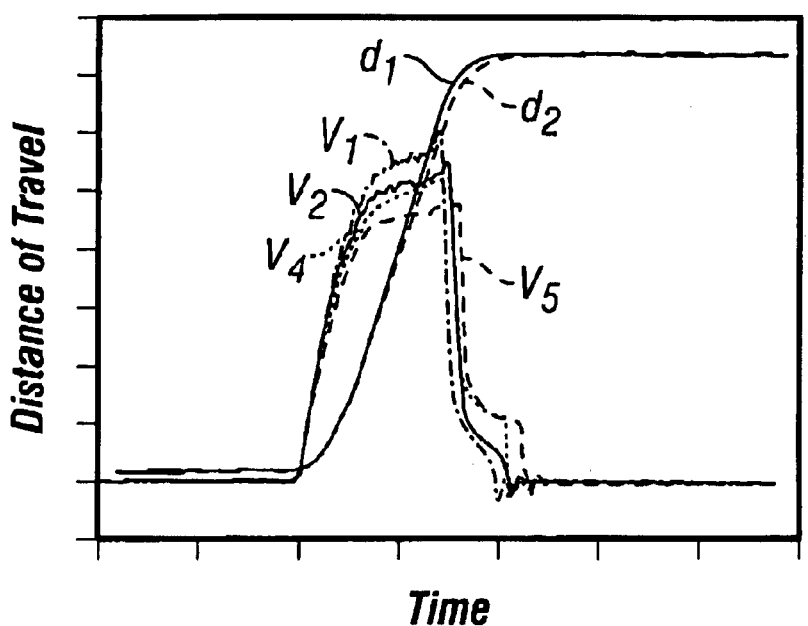
FIG. 2 shows the curves representing the change, in relation to time, of the distance of travel and velocity of an object, with which it is possible to understand the method of the invention.
Figure 3:
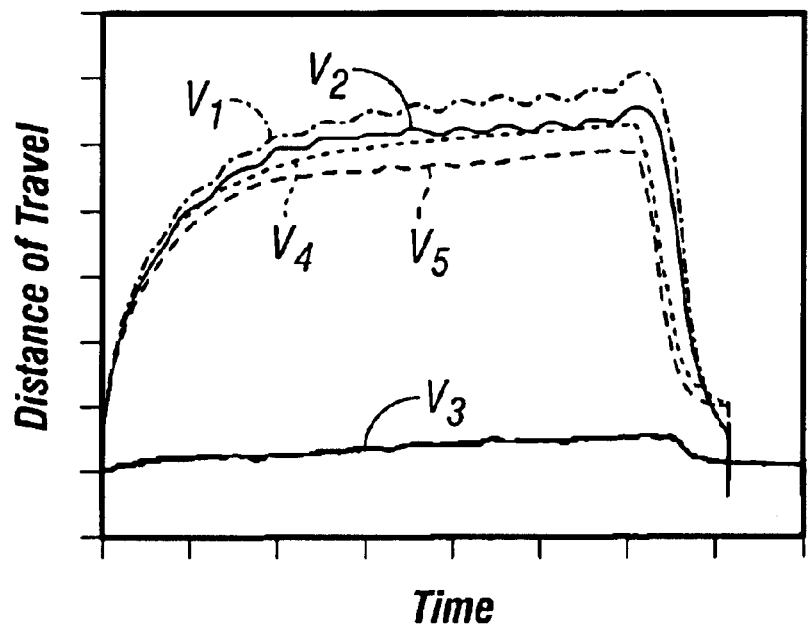
FIG. 3 shows the curves representing the change in velocity of an object in relation to distance of travel.
Figure 4:
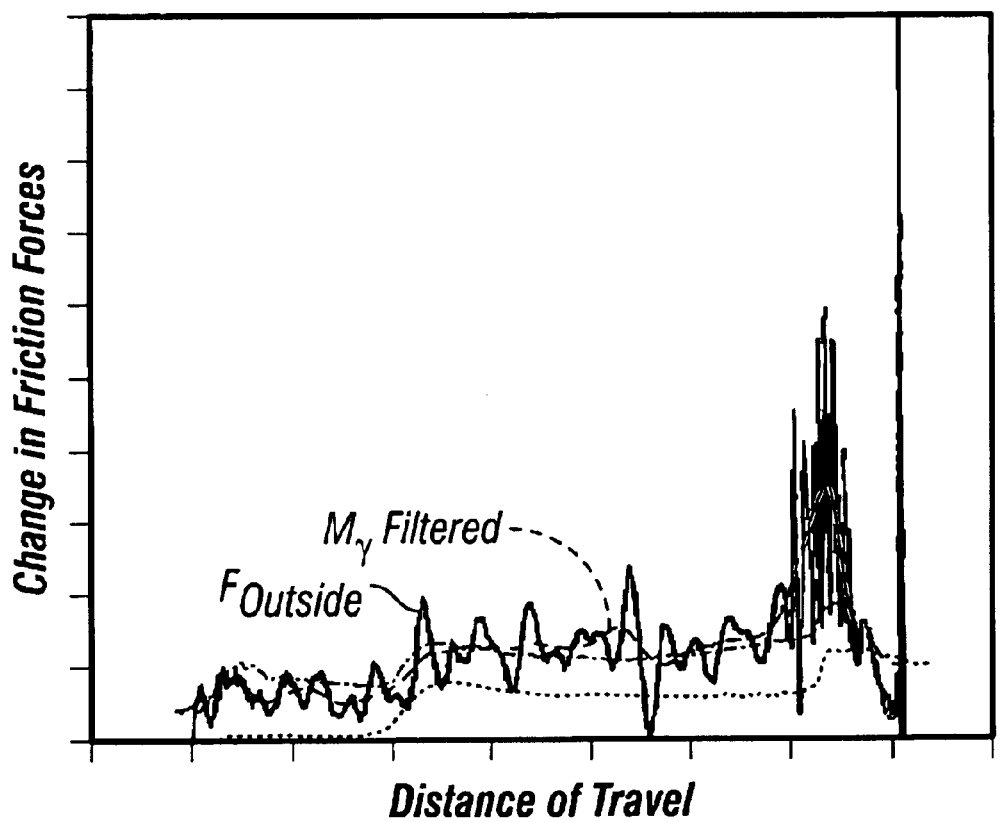
FIG. 4 shows the curves representing the change in forces in relation to distance of travel, assessed using the method of the invention.

The curves shown in FIGS. 2, 3 and 4 help to better understand the approach of the method according to the invention.

In FIG. 2, time is shown along the X-axis while velocity and distance of travel are both on the Y-coordinate. If only a slight variation is observed between the two curves representing the reference distance of travel denoted $d_1$ and deteriorated distance of travel $d_2$, the variations in velocity are more significant. In respect of the latter, it is observed that the two measured velocities $V_1$ and $V_2$ are greater than the calculated velocity $V_4$ and the velocity $V_5$ obtained at the end of the method. Evidently, it is ascertained that the deteriorated velocity $V_2$ is slower than the reference velocity $V_1$. In addition, it is found that this difference between $V_1$ and $V_2$ is transferred to $V_4$ and $V_5$. Moreover, this velocity difference $V_3$ between $V_1$ and $V_2$ appears in the graph in FIG. 3 in which the same remarks apply.

In FIG. 4, which shows the change in friction forces (Y-axis) in relation to distance of travel (X-axis), only the two curves having the greatest variations are to be taken into consideration. This figure shows the results of the method of the invention, that is to say the additional friction forces calculated during the last step of the method of the invention, step 8, and these same additional friction forces when filtered. The two other curves concern measured forces.

What is claimed is:

1. Method for determining friction forces occurring on a moving object in a guide, using a speed sensor, comprising the following steps of a calculation process:

1) measuring and recording changes in the velocity $V_1$ of the object initially before the occurrence of friction:

$$V_1=f_1(t),$$

wherein $f_1$ is a function of time (t);

2) calculating distance of travel $d_1$ with integrated change in velocity of the object before the onset of friction, to obtain the change in velocity, $V_1=g_1(d)$ in relation to distance of travel:

$$d_1(t) = \int_{u=0}^{t} V(u)\,du,$$

wheein $g_1$ is a second function of distance (d), and (u) is a time value;

3) measuring and recording the change in velocity $V_2$ of the object after the onset of friction:

$$V_2=f_2(t);$$

4) calculating distance of travel $d_2$ with integrated change in velocity of the object, after onset of friction, to obtain the change in velocity $V_2=g_2(d)$ relation to distance of travel;

$$d_2(t) = \int_{u=0}^{t} V_2(u)\,du;$$

5) calculating the difference of velocity $V_3$ between the two velocities $V_1$ and $V_2$ in relation to travel before and after onset of additional friction, $F_{additional}$;

6) calculating the change in velocity $V_4$ of the object in relation to distance of travel, before the onset of friction, using a predetermined calculation program, wherein $$V_4=g_4(d);$$

7) subtracting the difference of velocity $V_3$ from this change in velocity $V_4$, the difference $V_3$ in measured velocity changes:

$$V_5=V_4-V_3=g_5(d);$$

to obtain the difference of velocity $V_5$; and 8) deducing, by differentiation between $V_4$ and $V_5$ and multiplication by the weight M, the additional friction forces acting on the movement of the object;

$$F_{additional}=M(\gamma 5-\gamma 4)=f(d), \text{ wherein}$$

$$\gamma_i = \frac{dV_i}{dt};$$

and wherein $\gamma$ is the acceleration of the object, and subscripts 4, 5 represent successive values in the said calculation process.

2. Method according to claim 1, applied to a pressurized water nuclear reactor, the moving object being a mobile assembly formed of a control rod and control cluster, the guide being the lowering channel, the speed sensor being a rod position indicator (RPI) used to measure velocity.

* * * * *